United States Patent
Bertrandias et al.

(10) Patent No.: US 12,338,477 B2
(45) Date of Patent: Jun. 24, 2025

(54) RECOVERY OF METHANE FROM SOLID DIGESTATES

(71) Applicants: L'Air Liquide, Société Anonyme pour l'Etude et l'Exploitation des Procédés Georges Claude, Paris (FR); Institut National de Recherche pour l'Agriculture, l'Alimentation et l'Environnement, Paris (FR)

(72) Inventors: Aude Bertrandias, Paris (FR); Ulysse Bremond, Paris (FR); Jean-Philippe Steyer, Paris (FR); Helene Carrere, Paris (FR)

(73) Assignees: L'Air Liquide, Société Anonyme pour l'Etude et l'Exploitation des Procédés Georges Claude, Paris (FR); Institut National de Recherche pour l'Agriculture, l'Alimentation et l'Environnement, Paris (FR)

( * ) Notice: Subject to any disclaimer, the term of this patent is extended or adjusted under 35 U.S.C. 154(b) by 653 days.

(21) Appl. No.: 17/323,484

(22) Filed: May 18, 2021

(65) Prior Publication Data
US 2021/0363550 A1 Nov. 25, 2021

(30) Foreign Application Priority Data
May 20, 2020 (FR) ...................................... 2005137

(51) Int. Cl.
C02F 1/00 (2023.01)
C02F 11/04 (2006.01)
C02F 11/12 (2019.01)
C12M 1/00 (2006.01)
C12M 1/107 (2006.01)
C12P 5/02 (2006.01)

(52) U.S. Cl.
CPC ............... *C12P 5/023* (2013.01); *C02F 11/04* (2013.01); *C02F 11/12* (2013.01); *C12M 21/04* (2013.01); *C12M 23/36* (2013.01); *C12M 23/58* (2013.01)

(58) Field of Classification Search
CPC ...... C12M 21/04; C12M 23/44; C12M 23/58; C12M 41/22; C12M 41/34; Y02E 50/10
USPC ...................................................... 435/294.1
See application file for complete search history.

(56) References Cited

U.S. PATENT DOCUMENTS

| 4,684,468 A | 8/1987 | De Baere |
| 2010/0021979 A1 | 1/2010 | Facey et al. |

FOREIGN PATENT DOCUMENTS

| EP | 0 131 319 | 1/1985 |
| WO | WO 00 70010 | 11/2000 |
| WO | WO 2010 094115 | 8/2010 |

OTHER PUBLICATIONS

Bremond, U. et al., Assessment of fungal and thermo-alkaline post-treatments of solid digestate in a recirculation scheme to increase flexibility in feedstocks supply management of biogas plants, Renewable Energy 149, 2020, 641-651.
Kaparaju, P.L.N. et al., Effects of temperature on post-methanation of digested dairy cow manure in a farm-scale biogas production system, Environmental Technology, 24, 2003, 1315-1321.
Menardo, S. et al., The methane yield of digestate: effect of organic loading rate, hydraulic retention time, and plant feeding, Bioresource Technology 102, 2011, 2348-2351.
Sambusiti, C. et al., Bioethanol fermentation as alternative valorization route of agricultural digestate according to a biorefinery approach, Bioresource Technology 212, 2016, 289-295.
Thygesen, O. et al., Residual biochemical methane potential (BMP) of concentrated digestate from full-scale biogas plants, Fuel 132, 2014, 44-46.
French Search Report for corresponding FR 2005137, Feb. 5, 2021.

*Primary Examiner* — Robert B Mondesi
*Assistant Examiner* — Mohammad Y Meah
(74) *Attorney, Agent, or Firm* — Yan Jiang

(57) ABSTRACT

Process for producing biogas from a digestate obtained from a digester, said process comprising a step of recovering the digestate at the outlet of a digester, a post-digester or a storage tank; a step of separating the digestate into a solid digestate and a liquid digestate; a step of introducing the solid digestate into at least one dosed tank; a step of anaerobic digestion in the tank with neither heating nor mixing; and a step of recovering the biogas at the tank outlet.

7 Claims, No Drawings

RECOVERY OF METHANE FROM SOLID DIGESTATES

CROSS-REFERENCE TO RELATED APPLICATIONS

This application claims the benefit of priority under 35 U.S.C. § 119 (a) and (b) to French Patent Application No. 2005137, filed May 20, 2020, the entire contents of which are incorporated herein by reference.

TECHNICAL FIELD

The present invention relates to production of biogas from a digestate obtained from a digester.

BACKGROUND

Biogas is the gas produced during the degradation of organic matter in the absence of oxygen (anaerobic fermentation), also known as methanization. The degradation may be natural, Ike that observed in swamps or in household rubbish dumps; however, the production of biogas can also result from the methanization of waste in a dedicated reactor, the conditions of which are controlled, known as a methanizer or digester, and then optionally in a post-digester, which is similar to the digester and which makes it possible for the methanization reaction to be pushed further.

The term "biomass" is applied to any collective of organic matter which is convertible into energy by way of this methanization procedure, examples being treatment station slurries, dung/liquid manures, agricultural residues, energy crops, food wastes, etc. In Europe, agricultural residues and energy crops (dedicated or intermediate) make up a large part of the biomass processed, especially in Germany and Austria, and then in France. In Germany, 15% of agricultural digesters are operated in mono-digestion, in other words with 100% crops. The majority of digesters mix the crops with dung/liquid manure (codigestion).

The digestate is the residue of the biomass after anaerobic digestion. The digestate is generally pastelike and rich in carbon, nitrogen, potassium, phosphorus and trace elements. It has renowned soil conditioning and/or fertilizing qualities, while being organic in origin and generating less odour than the conventionally spread liquid manures or dung. The spreading of the digestate follows a strictly confined procedure.

The digester, that is to say the reactor dedicated to the methanization of biomass, is a closed vessel which is or is not heated (operation at a set temperature, between ambient temperature and 55° C.) and the contents of which, constituted by biomass, are stirred, continuously or sequentially. The conditions in the digester are anaerobic and the biogas generated is found in the headspace of the digester (gas headspace), where it is withdrawn. Post-digesters are similar to digesters.

Owing to its main constituents—methane and carbon dioxide—biogas is a powerful greenhouse gas; at the same time, it also constitutes a source of renewable energy, which is appreciable in the context of the increasing scarcity of fossil energy sources.

Biogas contains predominantly methane ($CH_4$) and carbon dioxide ($CO_2$), in proportions which can vary according to the way in which the biogas is obtained and to the substrate, but can also contain, in smaller proportions, water, nitrogen, hydrogen sulfide ($H_2S$) and oxygen, and also other organic compounds, in the form of traces, including the $H_2S$ at between 10 and 50 000 ppmv.

Depending on the organic matter that has been degraded and on the techniques used, the proportions of the components differ, although on average biogas includes, on a dry gas basis, from 30% to 75% methane, from 15% to 60% $CO_2$, from 0 to 15% nitrogen, from 0 to 5% oxygen and trace compounds.

Biogas is put to profitable use in various ways. After slight treatment, it may be utilized close to the site of production, to supply heat, electricity or a combination of the two (cogeneration).

Starting from this, a problem which is posed is that of improving the production of biogas.

SUMMARY

A solution of the present invention is a process for producing biogas from a digestate, said process comprising:
  a) a step of recovering the digestate at the outlet of a digester, a post-digester or a storage tank;
  b) a step of separating the digestate into a solid digestate and a liquid digestate;
  c) a step of introducing the solid digestate into at least one closed tank;
  d) a step of anaerobic digestion in the tank with neither heating nor mixing, and
  e) a step of recovering the biogas at the tank outlet.

Alternatively expressed, the solution according to the invention allows for recovery of the residual biogas generated by the solid digestate.

According to particular case, the process according to the invention may exhibit one or more of the following features:
  the anaerobic digestion step is carried out with inertizing of the tank with $CO_2$ or nitrogen;
  the anaerobic digestion step has a duration of between 1 and 6 months;
  the process is carried out during the summer months and the digestion step has a duration of between 1 and 4 months;
  the process is carried out during the winter months and the digestion step has a duration of between 3 and 6 months; the tank is a concrete tank closed with a rigid or flexible cover allowing the tank to be sealed tight after it has been closed;
  steps c) and d) employ at least two tanks in parallel;
  the amount of biogas produced from the solid digestate is measured at each time in step d), and this amount is compared to a target value, and the anaerobic digestion of the solid digestate is halted when the amount of biogas produced is greater than this target value. This allows the amount of biogas generated to be increased while retaining the agronomic qualities of the solid digestate (especially a sufficient carbon content for it to be made into a good conditioner); and
  the target value is between about 25 and 400 $Nm^3$ of biogas per tonne of volatile matter, preferably between about 100 and 300 $Nm^3$ of biogas per tonne of volatile matter.

A further subject of the present invention is a process for producing biogas from biomass, comprising:
  a) a step of introducing biomass into a digester and/or a post-digester;
  b) a step of anaerobic digestion in the digester and/or the post-digester;
  c) a step of producing a first stream of biogas and digestate;

d) a step of separating the digestate into a solid digestate and a liquid digestate;

e) a step of introducing the solid digestate into at least one closed tank;

f) a step of anaerobic digestion in the tank with neither heating nor mixing;

g) a step of recovering a second stream of biogas at the tank outlet; and h) a step of mixing the first stream of biogas and the second stream of biogas so as to form a stream M.

The process for producing biogas from biomass enables digester biogas yields to be improved, as it allows for recovery of the residual biogas. Moreover, this ameliorates the environmental impact of the digester, as there are no greenhouse gas emissions into the atmosphere obtained from the solid digestate.

According to particular case, the process for producing biogas from biomass exhibits one or more of the features below:

the stream M is purified so as to recover biomethane and $CO_2$ and step f) is performed with inertizing of the tank with the $CO_2$ obtained from the purification of said mixed stream;

step f) is performed with inertizing of the tank with nitrogen;

the process for producing biogas from biomass comprises a step of introducing the liquid digestate into a storage tank, a step of anaerobic digestion in this storage tank and a step of recovering a third stream of biogas at the outlet of this storage tank; and the third stream of biogas is mixed into the stream M.

Lastly the process for producing biogas from biomass further comprises a step for cogenerating heat and electricity from the stream M.

DESCRIPTION OF PREFERRED EMBODIMENTS

Within the invention, a solid digestate is introduced into a preferably concrete tank with a size of between 100 and 1000 $m^3$. In one embodiment, the tank may be closed with a rigid or flexible cover allowing the tank to be sealed tight after it has been closed. No heating or stirring system is incorporated. In one embodiment, loading of the solid digestate into the tank may be performed manually by tractors already present on site if the tank is situated at a distance from the separator of the digestate into liquid digestate and solid digestate. If, in contrast, the tank is at the base of the phase separator, loading may be operated simply by gravity, Subsequently, anaerobic digestion may proceed:

(i) slowly, with natural inertizing over time, (ii) or with inertizing by $CO_2$, preferably $CO_2$ obtained from the purification of the biogas, (iii) or with inertizing using nitrogen, preferably nitrogen from an external supply.

For the anaerobic digestion, the solid digestate may be left in the closed tank for 1 to 6 months: 1 to 4 months during the summer months and 3 to 6 months during the winter months, owing to the slower kinetics at low temperature. Note that a plurality of tanks may be used in parallel, to process a larger fraction of the solid digestate produced.

After the anaerobic digestion, the second stream of biogas generated by the solid digestate may be recovered at the top of the tank and mixed with the first stream of biogas generated by the digester. Said mixture may then be purified/cogenerated.

The tank itself may then be emptied by means for example of a tractor.

The solution according to the invention thus enables recovery, at lower cost, of the residual biogas from the solid digestate, without affecting the operation of the methanizer. This solution is of advantage especially when the digester is operating at maximum capacity and hence when the digestate cannot be recirculated. Moreover, this improves the carbon balance of a methanization site, by limiting the discharges of greenhouse gas and pollutants into the atmosphere (nitrogen dioxide and carbon dioxide, ammonia).

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and the include plural referents, unless the context clearly dictates otherwise.

As used herein, "about" or "around" or "approximately" in the text or in a claim means ±10% of the value stated.

"Comprising" in a claim is an open transitional term which means the subsequently identified claim elements are a nonexclusive listing i.e. anything else may be additionally included and remain within the scope of "comprising." "Comprising" is defined herein as necessarily encompassing the more limited transitional terms "consisting essentially of" and "consisting of"; "comprising" may therefore be replaced by "consisting essentially of" or "consisting of" and remain within the expressly defined scope of "comprising".

"Providing" in a claim is defined to mean furnishing, supplying, making available, or preparing something. The step may be performed by any actor in the absence of express language in the claim to the contrary.

Reference herein to "one embodiment" or "an embodiment" means that a particular feature, structure, or characteristic described in connection with the embodiment may be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used herein, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations, That is, if X employs A; X employs B; or X employs both A and B, then "X employs A or B" is satisfied under any of the foregoing instances.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range. Any and all ranges recited herein are inclusive of their endpoints (i.e., x=1 to 4 or x ranges from 1 to 4 includes x=1, x=4, and x=any number in between), irrespective of whether the term "inclusively" is used.

All references identified herein are each hereby incorporated by reference into this application in their entireties, as well as for the specific information for which each is cited.

Although the subject matter described herein may be described in the context of illustrative implementations to process one or more computing application features/operations for a computing application having user-interactive components the subject matter is not limited to these particular embodiments. Rather, the techniques described herein may be applied to any suitable type of user-interactive component execution management methods, systems, platforms, and/or apparatus.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

While embodiments of this invention have been shown and described, modifications thereof may be made by one skilled in the art without departing from the spirit or teaching of this invention. The embodiments described herein are exemplary only and not limiting. Many variations and modifications of the composition and method are possible and within the scope of the invention. Accordingly the scope of protection is not limited to the embodiments described herein, but is only limited by the claims which follow, the scope of which shall include all equivalents of the subject matter of the claims.

What is claimed is:

1. A process for producing biogas from a digestate obtained from a digester, wherein the biogas predominantly contains methane and $CO_2$ and also contains in smaller proportions of water, nitrogen, hydrogen sulfide and oxygen than the proportions of methane and $CO_2$, said process comprising the steps of:

a) introducing biomass into a digester and/or a post-digester;
b) anaerobic digestion in the digester and/or a post-digester;
c) producing a first stream of biogas and digestate;
d) separating the digestate into a solid digestate and a liquid digestate;
e) introducing the solid digestate into at least one closed tank in parallel;
f) anaerobic digesting the solid digestate in the closed tank with neither heating nor mixing; and
g) recovering the biogas at the closed tank outlet, wherein the anaerobic digesting step is carried out with a step of inertizing of the tank with $CO_2$ obtained from the anaerobic digesting the solid digestate, wherein steps e) and f) employ at least two tanks in parallel, wherein the amount of the biogas produced by the anaerobic digesting the solid digestate is measured at step f), wherein the measured amount of the biogas produced by the anaerobic digesting the solid digestate is compared to a target value of the amount of the biogas, wherein the step of the anaerobic digesting the solid digestate is halted when the each measured amount of biogas produced by the anaerobic digesting the solid digestate is greater than the target value.

2. The process for producing biogas of claim 1, wherein the anaerobic digesting step has a duration of between 1 and 6 months.

3. The process for producing biogas of claim 2, wherein the process is carried out during a temperature higher than ambient temperature and the anaerobic digesting step has a duration of between 1 and 4 months.

4. The process for producing biogas of claim 2, wherein the process is carried out during a temperature lower than ambient temperature and the anaerobic digesting step has a duration of between 3 and 6 months.

5. The process for producing biogas of claim 4, wherein that the tank is a concrete tank closed with a rigid or flexible cover allowing the tank to be sealed tight after it has been closed.

6. The process for producing biogas of claim 1, wherein the target value is from about 50 to about 400 $Nm^3$ of biogas per tonne of volatile matter.

7. The process for producing biogas of claim 1, wherein the target value is from about 100 to about 300 $Nm^3$ of biogas per tonne of volatile matter.

* * * * *